(12) United States Patent
Lin

(10) Patent No.: US 6,777,230 B2
(45) Date of Patent: Aug. 17, 2004

(54) PROSTATE CANCER CELL LINES

(75) Inventor: Ming-Fong Lin, Omaha, NE (US)

(73) Assignee: Board of Regents of the University of Nebraska, Lincoln, NE (US)

(*) Notice: Subject to any disclaimer, the term of this patent is extended or adjusted under 35 U.S.C. 154(b) by 0 days.

(21) Appl. No.: 09/919,196

(22) Filed: Jul. 31, 2001

(65) Prior Publication Data

US 2003/0027227 A1 Feb. 6, 2003

(51) Int. Cl.$^7$ ................................................ C12N 5/02
(52) U.S. Cl. .................. 435/325; 435/366; 435/371; 435/172.3; 424/93.1; 424/93.7
(58) Field of Search .............................. 424/93.1, 93.7; 435/325, 366, 371, 172.3

(56) References Cited

PUBLICATIONS

Embleton et al (Immunol Ser, 1984, 23:181–207).*
Hsu (in Tissue Culture Methods and Applications, Kruse and Patterson, Eds, 1973, Academic Press, NY, see abstract, p. 764).*
Mustafa Ozen et al, 1996, Intl J Oncology, 8(5): 883–888.*
Masters, J R et al, PNAS, USA, 2001, 98(14):8012–8017.*
Burchardt, T et al, 1999, J. Urol, 162(5): 1800–5.
Abrahamsson, P.–A, "Neuroendocrine cells in tumor growth of the prostate." Endocrine–Related Cancer 6: 503–519 (1999).
Cox, Michael E., et al., "Activated 3', 5'–Cyclic AMP–dependent Protein Kinase Is Sufficient to Induce Neuroendocrine–like Differentiation of the LNCaP Prostate Tumor Cell Line." J Biol Chem, 275(18): 13812–13818 (2000).
Noordzij, M. A., et al., "Neuroendocrine cells in the normal, hyperplastic and neoplastic prostate." Urol Res 22: 333–341 (1995).
Abrahamsson, P.–A. and H. Lilja, "Partial Characterization of a Thyroid–Stimulating Hormone–like Peptide in Neuroendocrine Cells of the Human Prostate Gland." The Prostate 14: 71–81 (1989).
Bonkhoff, Helmut, et al., "Relation of Endocrine–Paracrine Cells to Cell Proliferation in Normal, Hyperplastic, and Neoplastic Human Prostate," The Prostate 19: 91–98.
P. J. Gkonos, et al., "Neuroendocrine peptides in the prostate," Urol Res 23: 81–87 (1995).
Cussenot, Olivier, et al., "Evaluation and Clinical Value of Neuroendocrine Differentiation in Human Prostatic Tumors." The Prostate Supplement 8: 43–51 (1998).
Ahlgren, G., et al., "Neuroendocrine Differentiation is not Prognostic of Failure After Radical Prostatectomy but Correlates with Tumor vol." Urology 56(6): 1011–1015 (2000).
di Sant'Agnese, P. Anthony., "Neuroendocrine cells of the prostate and neuroendocrine differentiation in prostatic carcinoma: A review of morphologic aspects."Urology 51(Supplement 5A): 121–124 (1998).

di Sant'Agnese, P. Anthony., "Neuroendocrine Differentiation in Prostatic Carcinoma: An Update." The Prostate Supplement 8: 74–79 (1998).
Jiborn, Thomas et al., "Neuroendocrine Differentiation in Prostatic Carcinoma During Hormonal Treatment." Urology 51(4): 585–589 (1998).
Aprikian, Armen G., et al., "Neuroendocrine Differentiation and the Bombesin/Gastrin–Releasing Peptide Family of Neuropeptides in the Progression of Human Prostate Cancer." The Prostate Supplement 8: 52–61 (1998).
Sehgal, Inder et al., "Neurotensin is an autocrine trophic factor stimulated by androgen withdrawal in human prostate cancer." Proc. Natl. Acad. Sci. 91: 4673–4677 (1994).
Bonkhoff, Helmut and Klaus Remberger. "Differentiation Pathways and Histogenetic Aspects of Normal and Abnormal Prostatic Growth: A Stem Cell Model." The Prostate 28: 98–106 (1996).
Bang, Y.–J., et al., "Terminal neuroendocrine differentiation of human prostate carcinoma cells in response to increased intracellular cyclic AMP." Proc. Natl. Acad. Sci. 91: 5330–5334 (1994).
Shen, Ruoqian, et al., "Transdifferentiation of Cultured Human Prostate Cancer Cells to a Neuroendocrine Cell Phenotype in a Hormone–Depleted Medium." Urol Oncol 3: 67–75 (1997).
Qiu, Yun, et al., "Etk/Bmx, a tyrosine kinase a pleckstrin––homology domain, is an effector of phosphatidylinositol 3'–kinase and is involved in interleukin 6–induced neuroendocrine differentiation of prostate cancer cells," Proc. Natl. Acad. Sci. USA 95: 3644–3649 (1998).
Cox, Michael E., et al., "Acquisition of Neuroendocrine Characteristics by Prostate Tumor Cells is Reversible," Cancer Research 59: 3821–3830 (1999).
Lin, Ming–Fong, et al., "Expression of Human Prostatic Acid Phosphatase Correlates with Androgen–stimulated Cell Proliferation in Prostate Cancer Cell Lines." J Biol Chem, 273(10): 5939–5947 (1998).
Meng, Tzu–Ching, et al., "Interaction between protein tyrosine phosphatase and protein tyrosine kinase is involved in androgen–promoted growth of human prostate cancer cells." Oncogene 19: 2664–2677 (2000).
Hertog, Jeroen den, et al., "Receptor protein tyrosine phosphatase α activates pp60$^{c-src}$ and is involved in neuronal differentiation." The EMBO Journal 12(10): 3789–3798.
Bjelfman, Catarina, et al., "Ear Activation of Endogenous pp60$^{src}$ Kinase Activity during Neuronal differentiation of Cultured Human Neuroblastoma Cells." Molecular and Cellular Biology 10(1): 361–370 (1990).

(List continued on next page.)

Primary Examiner—Susan Ungar
Assistant Examiner—Minh Tam Davis
(74) Attorney, Agent, or Firm—Dann, Dorfman, Herrell and Skillman

(57) ABSTRACT

Novel human prostate cancer-associated neuroendocrine (NE)-like cell lines are provided that were derived via a process that resembles clinical androgen ablation therapy for advanced prostate cancer.

2 Claims, 10 Drawing Sheets

OTHER PUBLICATIONS

Lynch, Sally A., et al., "Induction of Altered c–*src* Product During Neural Differentiation Embryonal Carcinoma Cells." Science 234: 873–876 (1986).

van Inzen, Wouter G., et al., "The role of receptor protein tyrosine phosphatase α in neuronal differentiation of embryonic stem cells." Developmental Brain Research 91: 304–307 (1996).

Yang, Xiaohang, et al., "Two Drosophila Receptor–like Tyrosine Phosphatase Genes are Expressed in a Subset of Developing Axons and Pioneer Neurons in the Embryonic CNS." Cell 67: 661–673 (1991).

Zelivianski, Stanislav, et al., "Expression of receptor protein tyrosine phosphatase α mRNA in human prostate cancer cell lines." Molecular and Cellular Biochemistry 208: 11–18 (2000).

Sap, J., et al., "Cloning and expression of a widely expressed receptor tyrosine phosphatase." Proc. Natl. Acad. Sci. USA 87: 6112–6116 (1990).

Daum, Gunter, et al., "Multiple Forms of the Human Tyrosine Phosphatase RPTPα Isozymes and Differences in Glycosylation." The Journal of Biological Chemistry 269(14): 10524–10528 (1994).

Dixon, Shannon C., et al., "The Control of Prostate–Specific Antigen Expression and Gene Regulation by Pharmacological Agents." Pharmacological Reviews 53(1): 73–91 (2001).

* cited by examiner

Figure 1A: LNCaP Cells

Figure 1B: NE-1-3 Cells

Figure 1C: NE-1-8 Cells

PROSTATE CANCER CELL LINES

Pursuant to 35 U.S.C. Section 202(c), it is acknowledged that the United States Government has certain rights in the invention described herein, which was made in part with funds from the National Institutes of Health Grant Nos. RO1 CA72274 and RO1 CA88184.

FIELD OF THE INVENTION

This invention relates to the fields of tissue culture and the treatment of human prostate cancer. More specifically, novel cell lines are provided which may be used to identify new biomarkers for prostate cancer progression.

BACKGROUND OF THE INVENTION

Several publications are referenced in this application by numerals in parentheses in order to more fully describe the state of the art to which this invention pertains. Full citations for these references are found at the end of the specification. The disclosure of each of these publications is incorporated by reference herein.

Prostatic carcinoma is the most common malignant disease among men in the Western world, and benign prostatic hyperplasia is the most prevalent benign disease (1). In Western countries, it is estimated that men have approximately a 10% chance of developing prostate cancer and a 3–4% chance of dying of causes directly related to carcinoma of the prostate. The annual incidence of prostate cancer continues to increase, and this type of cancer now accounts for approximately 28% of all cancers in American men, compared to 18% in 1980 (1).

NE cells are a normal component of both the developing and mature prostatic epithelium. They produce a variety of neurosecretory products that exhibit growth-promoting activities, including parathyroid hormone-related peptides, neurotensin, serotonin, calcitonin and bombesin-related peptides, which suggests that these cells function through endocrine/paracrine mechanisms to regulate normal development and secretory activity of the prostate (2).

In a normal prostate, NE cells are distributed throughout the tissue and are readily detectable by microscopy as morphologically heterogeneous cells with irregular neurite-like processes extending between epithelial cells which often protrude into the lumen. NE cells may also be detected in prostate tissue by the presence of dense secretory vesicles (4–6). In prostate tumor tissue, NE cells often localize in clusters which increase in number with tumor progression (7).

Androgen ablation therapy (also known as hormonal deprivation therapy) is a well-established form of treatment for various stages of prostate cancer, especially advanced stages of cancer. However, this treatment alone does not cure the disease. During the course of androgen ablation therapy, prostate cancer cells will eventually lose their dependency on androgen and become highly aggressive. The molecular mechanism underlying this transition remains largely unknown. One hypothesis is that androgen ablation may result in the expansion of NE cells which in turn enhances the aggressiveness of the surrounding tumor cells because the NE cells secrete growth and motility promoting factors (3–5, 8–10).

Jiborn et al. (11) have shown that a marked increase in NE cell number is correlated with histopathologic tumor progression during androgen deprivation therapy, which suggests that resistance to hormonal therapy in prostate cancer may result from clonal proliferation of NE tumor cells. Interestingly, the proliferative index of neoplastic epithelial cells surrounding the NE cells is also often increased, which indicates that NE cells may act in a paracrine fashion by secreting growth-promoting factors, e.g., bombesin and neurotensin (12, 13).

Additionally, Bonkhoff et al. (14) have indicated that increases in the number of NE cells in prostate carcinomas occur either as a result of an increase in the stem cell population, which gives rise to NE cells in basal cells of normal prostate tissue, or by a process of trans-differentiation from malignant epithelial cells. The latter process may occur as tumor cells undergo de-differentiation steps (which are hallmarks of malignancy) and then, under certain circumstances, such as stimulation by differentiation inducing factors, a fraction of multipotent cells enter into a trans-differentiation program which results in the increase in NE cell population. The NE cells that undergo trans-differentiation may also be involved in hormone-refractory growth of prostate cancer. Alternatively, the population of NE cells may merely correlate with tumor volume (7).

Although there are a number of hypotheses describing the mechanism by which the NE cell population increases in the prostate, all of the possible mechanisms suggest that NE cells are associated with tumor growth.

SUMMARY OF THE INVENTION

In accordance with the present invention, novel human prostate cancer-associated neuroendocrine (NE)-like cell lines have been established.

The NE-like cells were derived from androgen-responsive LNCaP human prostate cancer cells by long-term culturing in an androgen-depleted condition which resembles conditions similar to androgen ablation therapy. LNCaP cells were initially seeded in regular medium containing phenol-red-positive RPMI 1640 medium supplemented with 5% regular fetal bovine serum for three days. Individual cells were seeded in a steroid-reduced medium containing phenol red-free RPMI 1640 medium supplemented with 5% heat-inactivated, charcoal/dextran-treated fetal bovine serum. The cells were then permitted to continue propagating in the steroid-reduced medium until the cells grew as independent cell lines.

The NE-like cell lines of the invention may be used to advantage to identify new biomarkers for prostate cancer progression. The identification of such biomarkers facilitates the development of novel therapeutic strategies for the treatment and prevention of prostate cancer.

BRIEF DESCRIPTION OF THE DRAWINGS

FIGS. 1A–1C show micrographs of the androgen-responsive human prostate cell line, LNCaP, and two NE-like subclone cells, NE-1-3 and NE-1-8.

FIG. 6A is a western blot wherein the expression of RPTPα in LNCaP cells and three NE-like subclone cells, NE-1-3, NE-1-8 and NE-1-9 was detected using immunospecific antibodies. FIG. 6B shows a western blot wherein the expression of ERK1 and ERK2, as well as phosphorylated ERK1 and ERK2, was immunospecifically detected in LNCaP cells, and two NE-like subclone cells, NE-1-3 and NE-1-8.

FIG. 7A is a western blot showing levels of MEK and phosphorylated MEK in LNCaP cells and three NE-like subclone cells, NE-1-3, NE-1-8 and NE-1-9. FIG. 7B is a western blot showing inhibition of ERK activation levels in the presence of the MEK inhibitor, PD098059, in NE-1-3 subclone cells. FIG. 7C is a western blot showing inhibition of NSE expression levels mediated by the MEK inhibitor, PD098059, in steroid-reduced medium.

FIG. 9A shows western blot resolution of NSE expression in LNCaP cells transfected with RPTPα cDNA. FIG. 9B shows a western blot wherein the expression of NSE, ERK1 and ERK2, as well as phosphorylated ERK1 and ERK2, was immunospecifically detected in LNCaP cells transfected with RPTPα cDNA.

DETAILED DESCRIPTION OF THE INVENTION

Figure 1D:
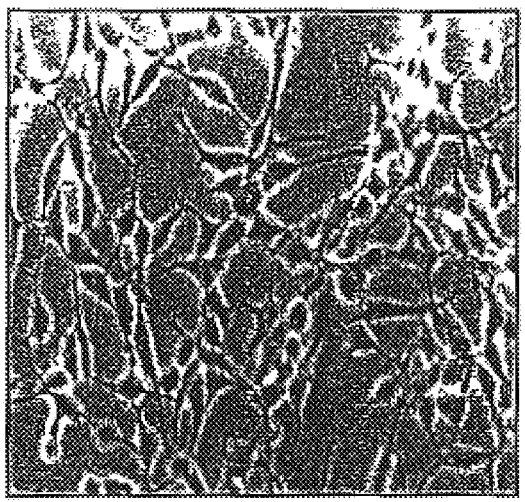
FIG. 1D shows a western blot of neuron-specific enolase (NSE) in each of these cell populations detected using enolase specific antibody. β-actin was used as a control.
Figure 1D:
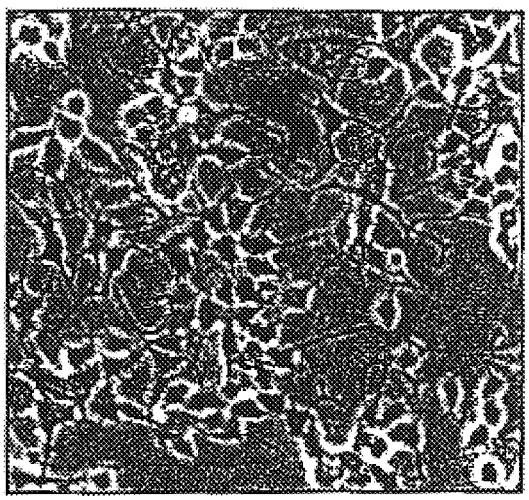
Figure 1D:
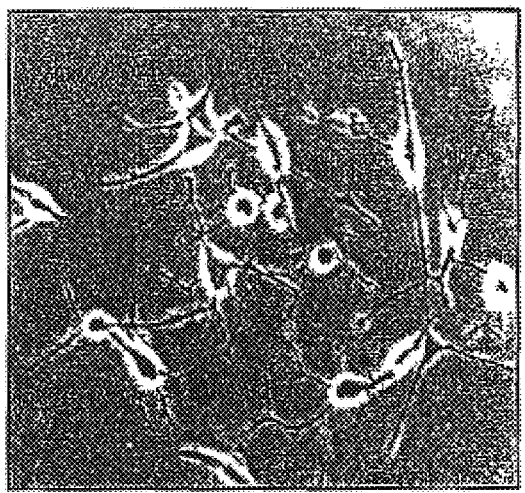
Figure 1D:
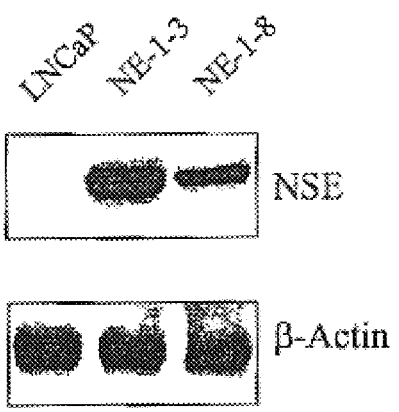

Neuroendocrine (NE) cells are involved in prostate cancer progression, and more specifically, may play a key role in androgen-refractory tumor growth. Therefore, due to the tremendous clinical importance of this form of cancer, it is imperative to clarify the functional role of NE cells in prostate carcinomas, especially in advanced hormone-refractory growth.

The androgen-responsive prostate tumor cell line, LNCaP, is a useful model for testing the development of NE cell phenotype in adenocarcinoma cells. LNCaP cells acquire NE characteristics in response to increased intracellular cAMP levels, long-term androgen ablation and stimulation with cytokines interleukin-1-β and interleukin-6 (15–17). However, maintenance of the NE phenotype is lost upon withdrawal of these differentiation-inducing agents, which results in the retraction of neuritic processes, reinitiation of mitotic activity, and loss of neuronal marker expression (18). Thus, the ability to study the molecular mechanism(s) of NE cells has been limited by the lack of a permanent experimental system that enables the examination of NE transdifferentiation in human prostate cells.

In accordance with the present invention, novel NE-like subclone cells have been derived from androgen-responsive LNCaP human prostate cancer cells by long-term culturing in an androgen-depleted condition which resembles conditions similar to androgen ablation therapy. These subclone cells provide a useful system which may be used to advantage to assess the functional role of NE cells in androgen-refractory growth of prostate cancer, and to investigate the molecular mechanism of transdifferentiation in prostate cancer cells.

I. Definitions:

The following definitions are provided to facilitate an understanding of the present invention:

A "clone" or "clonal cell population" is a population of cells derived from a single cell or common ancestor by mitosis.

A "cell line" is a clone of a primary cell or cell population that is capable of stable growth in vitro for many generations.

Prostate cells are "androgen responsive" if their growth is stimulated by "androgens" or hormones produced by the sex organs and adrenal glands.

"Androgen refractory tumor growth" refers to the condition wherein normally androgen-dependent prostate cells become prostate tumor cells that do not depend on androgen for their proliferation.

"Androgen ablation therapy" is one form of prostate cancer treatment whereby anti-androgens are administered to block the interaction between androgens and their receptors in the presence of normal or even increased target tissue.

"NE-like" cells refers to a population of cells derived from LNCaP human prostate cancer cells following long-term culture in an androgen-depleted condition. NE-like cells express high levels of marker proteins that are typically expressed in normal NE cells and are associated with aggressive progression of prostatic carcinomas.

II. Cell Lines:

In a preferred embodiment, cell lines of the invention are derived from the LNCaP cell line which is an immortalized, human, androgen-responsive prostate tumor cell line.

In yet another embodiment of the invention, cell lines of the invention may be derived from human prostate epithelial tumor cell lines PC-3 and DU145.

III. Exemplary Cell Lines:

Exemplary cell lines of the present invention are the NE-like subclone cell derivatives of LNCaP, referred to as NE-1-3, NE-1-8 and NE-1-9.

IV. Uses of the NE-like Subclone Cells:

The NE-like subclone cells of the present invention provide a superior cell based system to investigate prostate cancer because: (1) there are no spontaneously transdifferentiated human prostate cancer cell lines presently available; (2) the cell lines are the only available NE cell lines derived from prostate cancer cells cultured in an environment that resembles clinical androgen ablation therapy; and (3) the cell lines facilitate elucidation of the role played by NE cells in tumor progression as well as hormone refractory growth of prostate cancer.

The NE-like subclone cells of the invention express NE-specific markers. Therefore, these cells will be beneficial for investigating the molecular mechanism(s) by which prostate cancer cells transdifferentiate into prostate cancer-associated NE cells, a critical phenomenon in prostate cancer therapy.

In one embodiment of the invention, NE-like subclone cells may be used to advantage to facilitate the development of therapeutic agents, such as immuno- and chemo-reagents, for the treatment of prostate cancer, as well as test the efficacy of therapeutic agents for advanced hormone-refractory human prostate cancer. For example, monoclonal antibodies may be generated that are specific for NE-like subclone cells, but not cancer cells. These antibodies may be used for immunotherapy and immunodiagnosis of prostate cancer. Additionally, the identified molecules which are involved in NE transdifferentiation may serve as targets for prostate cancer therapy by developing specific inhibitors that block NE transdifferentiation.

In another embodiment of the invention, the NE-like subclone cells may be used to advantage to identify functional genes that are involved in prostate cancer progression during androgen ablation therapy. Such genes may be used as biomarkers for predicting prostate cancer progression as well as to facilitate determination of which therapeutic reagents should be used to treat specific cases of prostate cancer based on the severity of the cancer's progression. Functional genes may be identified using standard DNA array approaches known to those of skill in the art. The candidate genes may also serve as targets for prostate cancer therapy by developing immuno- and chemo-reagents that modulate gene expression.

V. Deposit of Clones NE-1-3 and NE-1-8:

A deposit of the NE-like subclones, NE-1-3 and NE-1-8, has been made with the American Type Culture Collection (ATCC), 10801 University Blvd., Manassas, Va. 20110, under the provisions of the Budapest Treaty for the International Recognition of the Deposit of cell lines for the purposes of patent procedure. The date of deposit was Jul. 27, 2001. NE-1-3 was accorded ATCC accession number PTA-3568 and NE-1-8 was accorded ATCC accession number PTA-3569.

The following example is provided to illustrate an embodiment of the invention. It is not intended to limit the scope of the invention in any way.

EXAMPLE 1

Human prostate NE-like subclone cell lines were established to facilitate the investigation of the functional role of prostate NE cells in hormone-refractory growth of cancer cells. The NE-like subclone cells were established by inducing NE transdifferentiation in androgen-responsive LNCaP cells under androgen-depleting conditions. This approach was chosen because clinical observations indicated that an increase in NE cell populations is correlated with prostate cancer progression during androgen ablation therapy (11–14).

Establishment of Prostate NE-like Subclone Cells

Androgen-responsive LNCaP cells were initially seeded by routine culturing at low density in a regular medium that contained phenol red-positive RPMI 1640 medium supplemented with 5% fetal bovine serum. Phenol red was added to the regular medium because it serves as a pH indicator of culture medium and also exhibits androgenic activity on LNCaP cells. After 3 days, the cells were fed with a steroid-reduced medium which contained phenol red-free RPMI 1640 medium supplemented with 5% heat-inactivated, charcoal/dextran-treated fetal bovine serum. The final concentration of testosterone in this medium was below 5 pM, and the Kd of androgens to its receptors was at nM concentration. Under these conditions, cell growth was diminished within the first week and was absent thereafter. The absence of cellular growth was accompanied by a striking morphologic change in cellular appearance. The cells were slightly smaller in body size and the cells developed much longer processes similar to those of cultured neuronal cells (data not shown).

A single surviving cell from this culture was cloned in a cylinder and propagated in the same steroid-reduced medium in an FNC coating mix$^R$-treated plastic flask. After several months of culturing, numerous individual cells grew and became independent cell lines. These subclone cells exhibited a similar neuronal cell phenotype. Two randomly selected subclone cells are shown in FIG. 1 (NE-1-3 and NE-1-8). The subclone cell lines have characteristic neuronal cell morphology: small cell bodies with long, irregular neurite-like processes, similar to that observed in cultured neuronal cells. Although the androgen-responsive LNCaP parental cells also exhibit processes, these processes are shorter with less processes per cell (FIG. 1).

Characterization of Biomarkers in NE-like Subclone Cells

The NE-like subclone cell lines were further characterized to determine the extent of their NE-like properties by measuring the expression of various NE-specific markers. The expression levels of the first marker, neuron-specific enolase (NSE) (15–17), was detected by western blot of lysates obtained from two subclone cell populations, NE-1-3 and NE-1-8 (FIG. 1). Both the NE-1-3 and NE-1-8 cells expressed NSE. Unexpectedly, the LNCaP parental cells also expressed NSE. However, the level of NSE expression in the LNCaP cells was much lower than the level of NSE expression in the NE-1-3 and NE-1-8 cells. As a control, the same membrane was hybridized with an anti-β-actin antibody to ensure that an equal amount of protein was loaded in each lane. After semi-quantifying and normalizing the NSE level in NE-1-3 and NE-1-8 cells to β-actin, the NSE protein level in the two NE-like subclone cells was approximately 20-fold higher than that in the LNCaP parental cells. This result suggests that prostate carcinoma cells and prostate NE cells may be derived from the same multipotent stem cells because both cell types express the specific NSE marker even though the prostate carcinoma cells express a much lower level of NSE.

Figure 2:
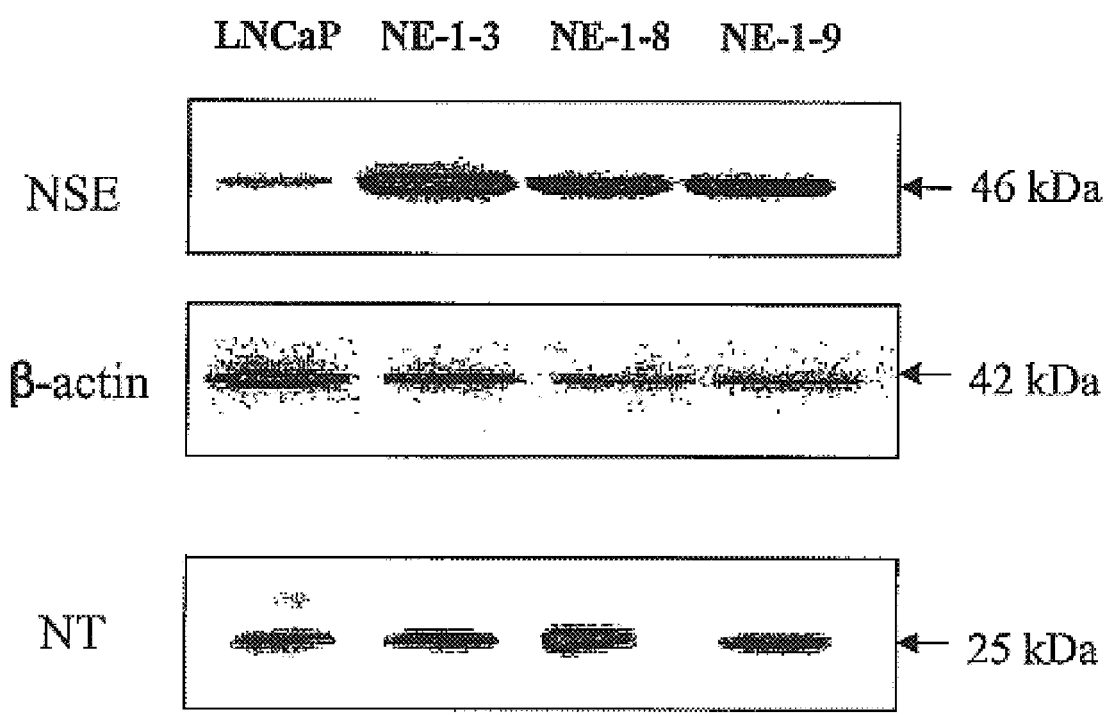
FIG. 2 shows western blots wherein the expression of NSE and NT in LNCaP cells and three NE-like subclone cells, NE-1-3, NE-1-8 and NE-1-9 was detected using appropriate immunospecific antibodies. β-actin was used as a control.

The expression of another marker, neurotensin (NT), was also examined in the three independent subclone cell lines, NE-1-3, NE-1-8 and NE-1-9. NT is often found associated with a variety of cancers, including prostate cancer. In each of the three independent subclone cell lines, NT expression was elevated by approximately 50–100% as compared to parental LNCaP cells, albeit at a lesser degree than NSE expression levels (FIG. 2). These results indicate that the NE-like subclone cells are similar to prostate NE cells in clinical prostate carcinomas because they both express NSE and NT. However, the established NE-like subclone cell lines differ from prostate NE cells in that the NE-like subclone cells are capable of proliferating under steroid-reduced conditions, whereas NE cells in normal prostate gland are histologically nonproliferative and represent a terminally differentiated cell population.

Figure 3:
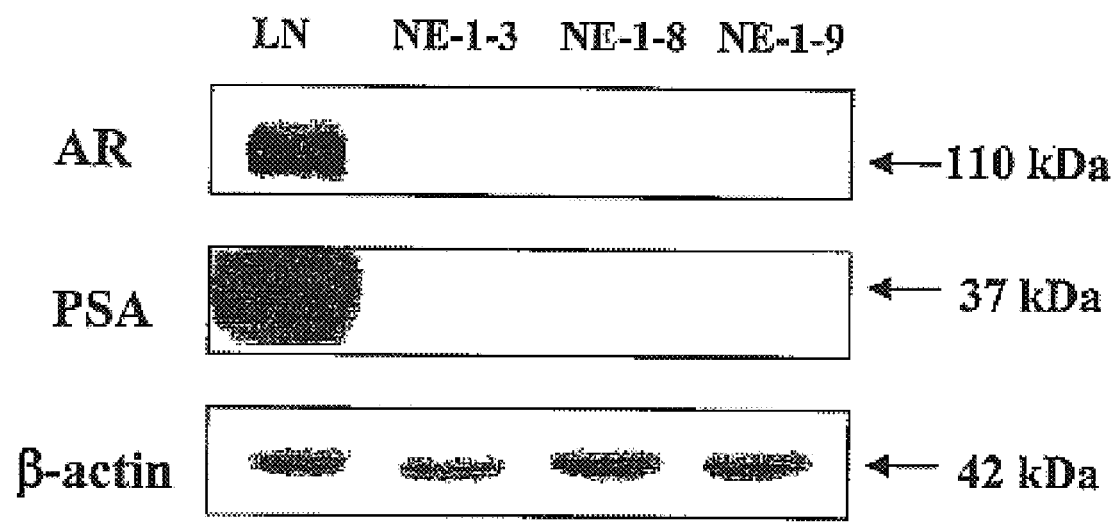
FIG. 3 shows western blots wherein the expression of two prostate cell markers, AR and PSA, in LNCaP cells and three NE-like subclone cells, NE-1-3, NE-1-8 and NE-1-9 was detected using appropriate immunospecific antibodies. β-actin was used as a control.

The expression of two additional biomarkers found on the parental LNCaP cell line, androgen receptor (AR) and prostate-specific antigen (PSA), were also analyzed in the NE-like subclone cells. After long-term culturing in an androgen-depleted condition (phenol red-free), the expression of AR and PSA was completely suppressed in all three NE-like subclone cells examined. This data suggests that AR and PSA expression is apparently androgen dependent (FIG. 3).

Figure 4A:
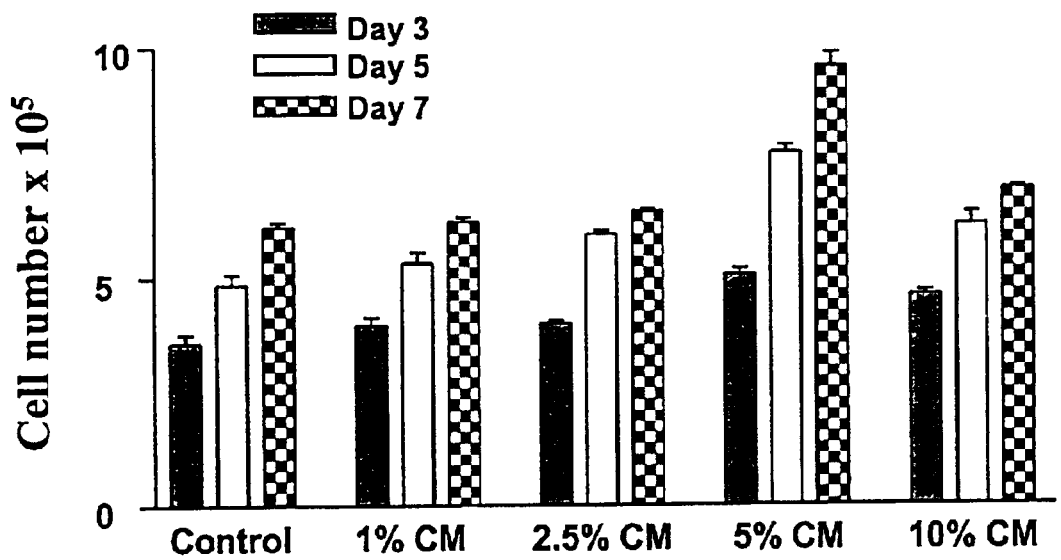
FIGS. 4A and 4B show two graphs illustrating the level of cellular growth of androgen-responsive LNCaP cells in NE-like subclone cell conditioned medium (FIG. 4A) and LNCaP conditioned medium (FIG. 4B).
Figure 4B:
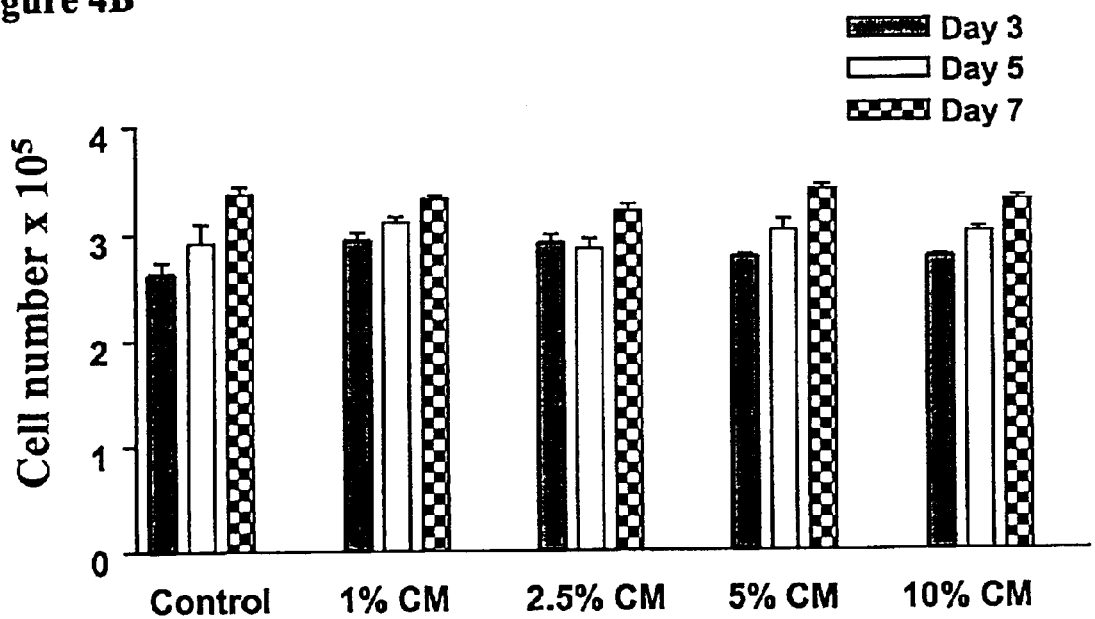

Effects of Conditioned Medium From NE-Like Cells on the Growth of Androgen-Responsive LNCaP Cells In order to elucidate the functional role of NE cells in the progression of hormone-refractory prostate cancer, conditioned medium from cultured NE-like subclone cells was tested to determine whether it contained factors which promote the growth of androgen-responsive prostate cancer cells under androgen-reduced conditions. Conditioned medium from cultured NE-1-3 cells (5 day culture) was collected after centrifugation to remove cell debris, adjusted to the neutral pH value and sterile filterized. The androgen-responsive LNCaP cells were seeded in regular medium for 2 days, followed by culturing in steroid-reduced medium for 2 days. The LNCaP cells were then maintained in fresh steroid-reduced medium in the presence of different concentrations of NE-1-3 subclone cell conditioned medium. As illustrated by the graphs presented in FIG. 4, NE-1-3 subclone cell conditioned medium promotes the growth of the androgen-responsive LNCaP cells. The conditioned medium stimulates growth in a bell-shaped dose response fashion (FIG. 4A). This bell-shaped phenomenon was previously observed during androgen stimulation of LNCaP cell growth (19). The 5% (v/v) NE-like subclone cell conditioned medium promoted the growth of LNCaP cells by more than 50% under androgen-reduced conditions. As a control, conditioned medium from the LNCaP parental cells was prepared following the same protocol. Interestingly, after maintaining the LNCaP cells in the LNCaP conditioned medium, there was no detectable effect on the growth of these cells (FIG. 4B). One possible explanation for these observations is that the NE-like subclone cells express and secret growth stimulating factors which promote the proliferation of androgen-responsive LNCaP cells in culture thereby providing a mechanism by which NE cells contribute to the progression of prostate cancer cells following androgen ablation therapy.

Molecular Signaling in NE-like Subclone Cells

Figure 5:
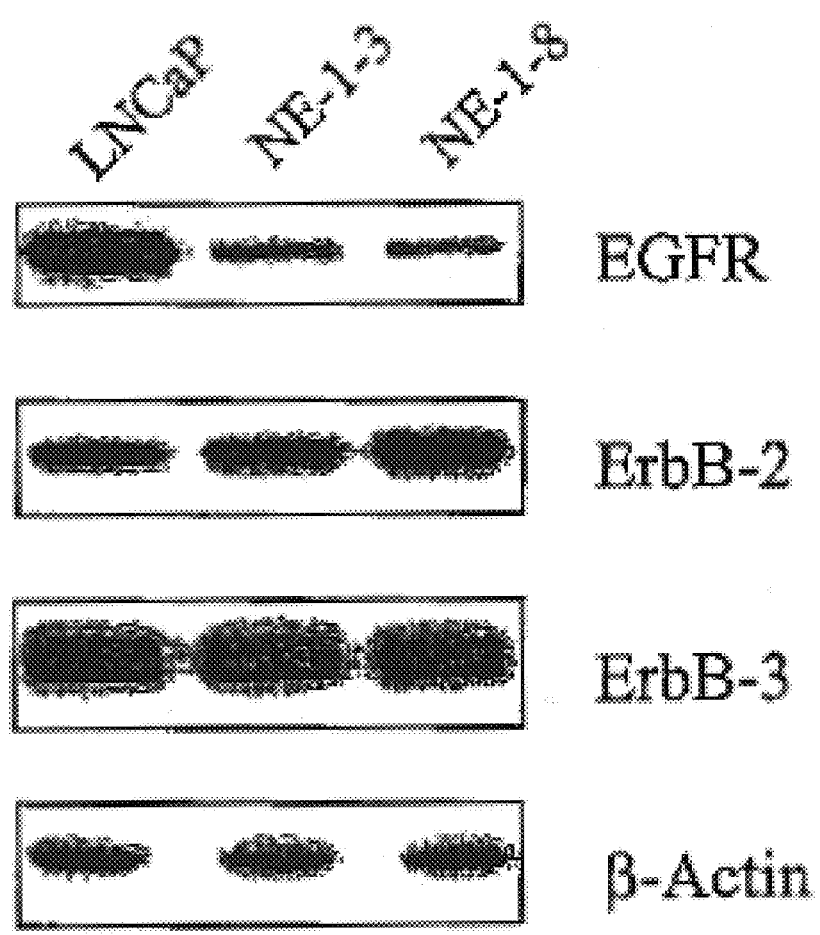
FIG. 5 shows western blots wherein the expression of EGFR, ErbB-2 and ErbB-3 in LNCaP cells and two NE-like subclone cells, NE-1-3 and NE-1-8, was detected using appropriate immunospecific antibodies. β-actin was used as a control.

To assess tyrosine phosphorylation signaling in the NE-like subclone cells, the expression levels of members of the erb family were determined by western blot since both epidermal growth factor receptor (EGFR) and ErbB-2 play critical roles in various aspects of growth regulation in prostate cancer cells (19, 20). Western blot analysis revealed a decrease in EGFR expression in NE-like subclone cells, an increase in ErbB-2 expression by approximately 50–100%, and no significant change in the level of ErbB-3 expression (FIG. 5).

Figure 6A:
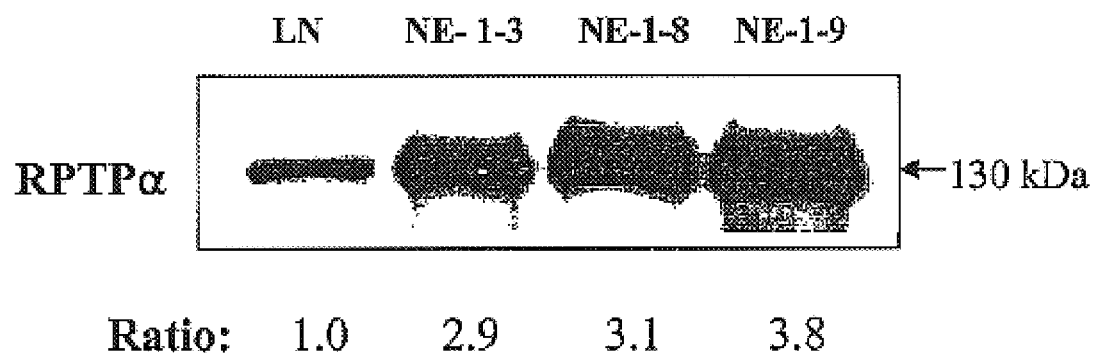
FIGS. 6A and 6B show two western blots.

The expression level of RPTPα was also examined. RPTPα is a receptor-type protein tyrosine phosphatase which has been shown to have a critical role in neuronal cell differentiation (21–25). The LNCaP parental cell line expresses RPTPα having a molecular mass of 130 kDa (26–28). NE-like subclone cells had exhibited higher levels of expression than the parental LNCaP cell line (FIG. 6A). Densitometric scanning indicated that the expression level of RPTPα was elevated approximately three to four fold in the NE-like subclone cells.

Figure 6B:
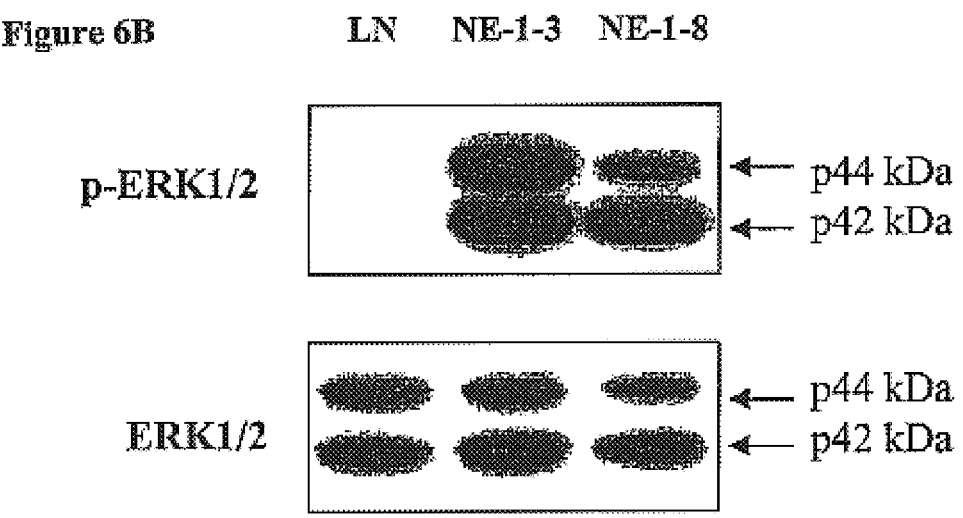

In addition to their functional role in cell proliferation, ERK/MAP kinases also play a critical role in neuronal cell differentiation. Thus, ERK/MAPK levels were examined to see if these kinases are involved in prostate NE transdifferentiation. Both ERK1 and ERK2 were highly activated, as indicated by their reactions with a specific antibody that recognizes activated, phosphorylated ERK/MAPKs (FIG. 6B). After stripping, the same membrane was then hybridized with an antibody to the unphosphorylated ERK/MAPK proteins. The results demonstrated that ERK/MAPKs are greatly activated in NE-like subclone cells (FIG. 6B) which suggests that these kinases play a role at the molecular level in NE cell transdifferentiation.

Figure 7A:
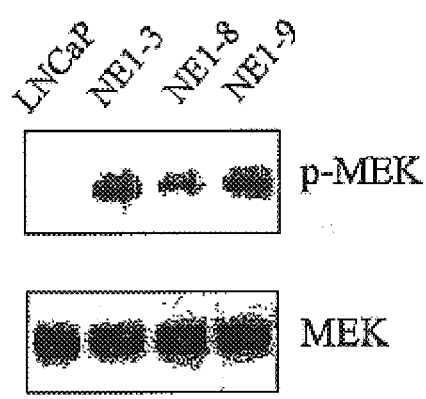
FIGS. 7A–7C show three western blots.
Figure 7B:
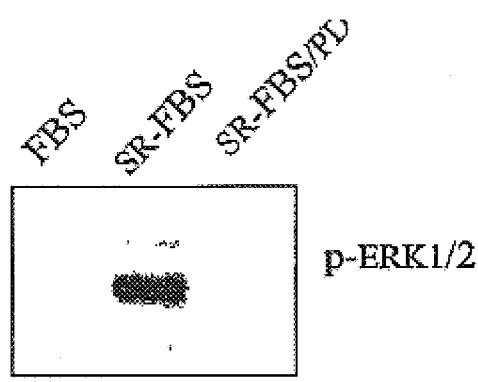
Figure 7C:
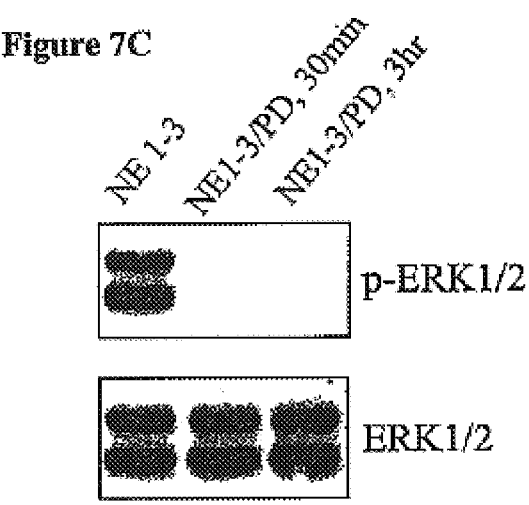
Figure 7C:
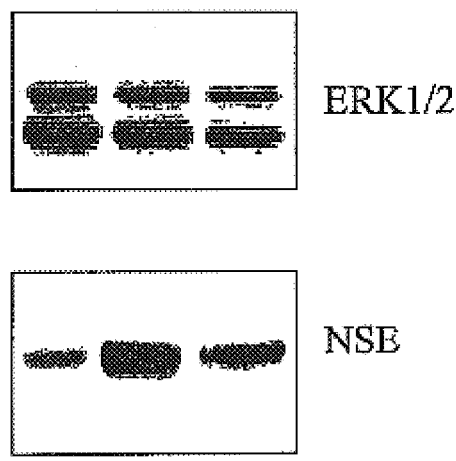

To test the causal relationship of ERK/MAPK activation with NE-like transdifferentiation, MEKs, up-stream regulators of ERK/MAPK kinases, were examined to determine if they are also activated in the NE-like subclone cells. The results showed that the MEKs were highly activated in the three independent NE-like subclone cells tested, which was demonstrated by their reaction with an antibody against phosphorylated MEKs (FIG. 7A). Additionally, the MEK inhibitor, PD098059, effectively inhibited the activation of ERK/MAPK in NE-like subclone cells, which indicated that MEK activation is necessary to activate ERK/MAPK (FIG. 7B). This inhibitor also abolished the induction of NE transdifferentiation during culturing of androgen-responsive LNCaP cells in a steroid-reduced condition, as demonstrated by the inhibition of NSE expression (FIG. 7C).

Figure 8:
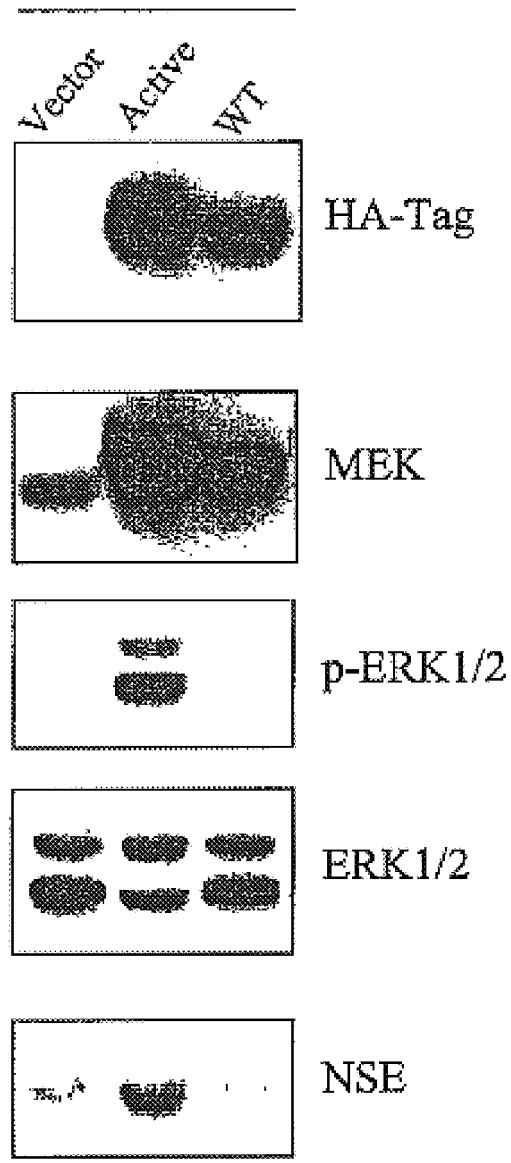
FIG. 8 shows western blots of constitutively activated ERK protein and elevated NSE protein level in androgen-responsive LNCaP cells following MEK cDNA transfection encoding a constitutively activated MEK protein.

In addition, forced expression of MEK was examined to see if it induces NE transdifferentiation in prostate cancer cells. Androgen-responsive LNCaP cells were transiently transfected with a cDNA encoding a constitutively activated MEK protein (labeled as "Active" in FIG. 8). Control cells were transfected with the vector alone or with a cDNA encoding the wild type (wt) protein which required activation by Raf protein. The results showed that an elevated expression level of constitutively active MEK was associated with activation of ERK/MAPK and an increase in NSE expression, while the wild type cDNA had no effect since it required activation by Raf (FIG. 8). Thus, activation of ERK/MAPK by forced expression of a constitutively activated MEK resulted in the elevation of NSE expression.

Figure 9A:
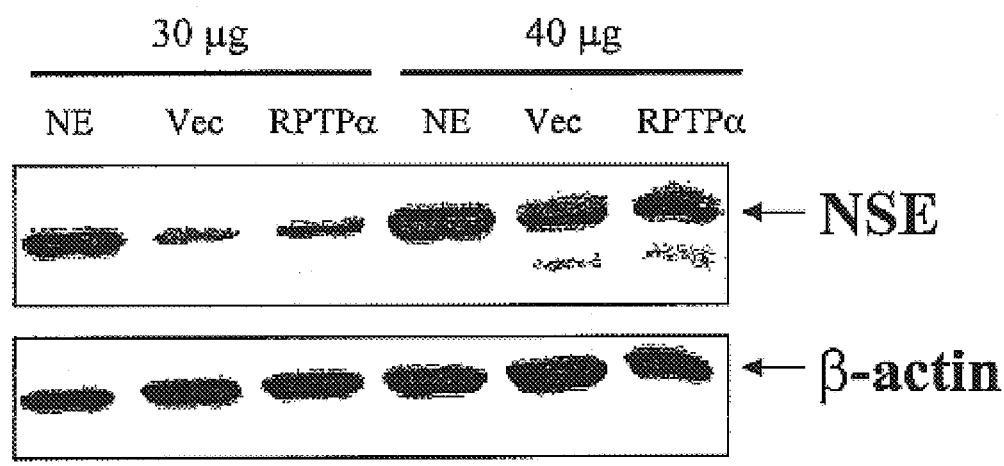
FIGS. 9A and 9B show two western blots.
Figure 9B:
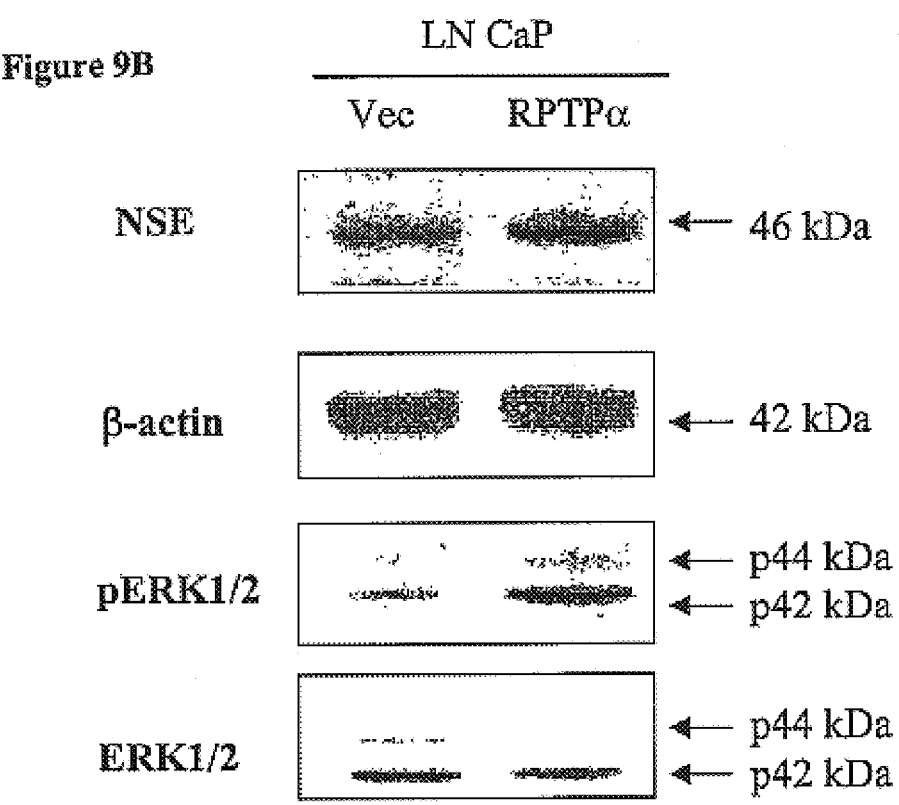

To directly examine whether there is a causal relationship between RPTPα expression and NE-transdifferentiation, androgen-responsive LNCaP cells were transfected with an RPTPα cDNA (donated by Dr. Tony Hunter, Salk Institute, Ca.) which resulted in increased expression of RPTPα correlated with an elevated level of NSE expression, and activation of ERK/MAPK (FIGS. 9A and 9B). This data suggests that RPTPα expression plays a role in NE differentiation of prostate cancer cells.

Figure 10A:
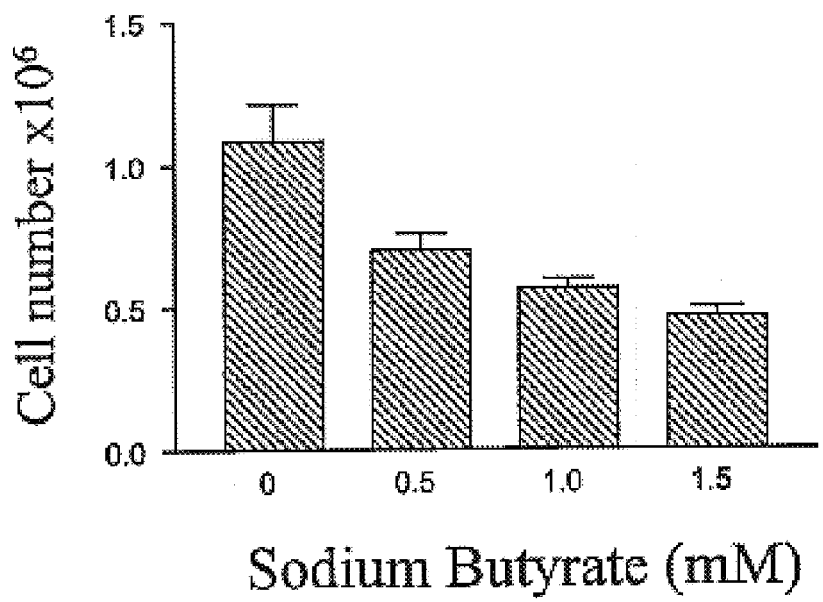
FIGS. 10A and 10B show a pair of graphs illustrating the effects of sodium butyrate on LNCaP cell population (FIG. 10A) accompanied by a western blot showing resolution of NSE and RPTPα expression levels in LNCaP cells in the presence of increasing concentrations of sodium butyrate (FIG. 10B).
Figure 10B:
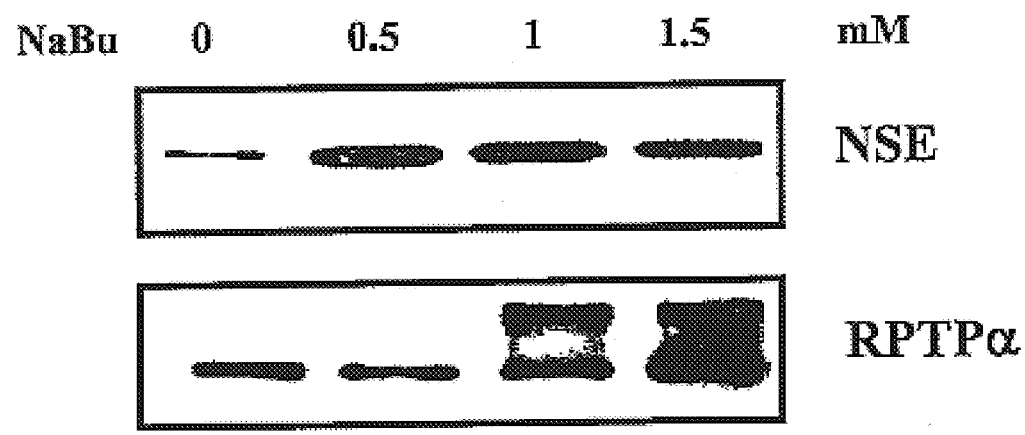

The regulation of RPTPα expression was then investigated in prostate cancer cells. The regulation of RPTPα expression was measured using butyrate since this pharmacological reagent induces cellular differentiation and has been utilized in the clinical trials for advanced prostate cancer therapy (29). Butyrate treatment resulted in growth suppression of LNCaP cells (FIG. 10A). However, western blot analyses revealed elevated levels of NSE and RPTPα protein expression (FIG. 10B), similar to those observed in the NE-like subclone cells (FIG. 6B). Interestingly, an additional 160 kDa protein also reacted with the antibody to RPTPα protein. This 160 kDa protein may represent an isoform of RPTPα, due to post-translational modifications (27, 28).

Based on the foregoing results, stable NE-like subclone cell lines that retain NE cell phenotype have been successfully established. These NE-like subclone cell lines provide a useful system to further characterize the molecular role of NE cells in human prostate cancer and may also be used to advantage to facilitate the development of novel therapeutic strategies for the treatment of this disease.

REFERENCES

1. Abrahamsson, P A (1999). Neuroendocrine cells in tumour growth of the prostate. Endocrine-Related Cancer. 6:503–519.
2. Cox, M E, Deeble, P D, Bissonette, E A, and Parsons S J (2000). Activated 3',5'-Cyclic AMP-dependent Protein Kinase is sufficient to induce Neuroendocrine-like differentiation of the LNCaP prostate tumor cell line. J. Biol. Chem. 275:13812–13818.
3. Noordzij, M A, Van Steenbrugge, G J, Van Der Kwast, T H, & Schroder, F H (1995). NE cells in the normal, hyperplastic and neoplastic prostate. Urol. Res. 22:333–341.

4. Abrahamsson, P A, & Lilja, H (1989). Partial characterization of a thyroid-stimulating hormone-like peptide in NE cells of the human prostate gland. Prostate, 14:71–81.
5. Bonkhoff, H. Wernert, N, Dhom, G, & Remberger, K (1991). Relation of endocrine-paracrine cells to cell proliferation in normal, and neoplastic human prostate. The Prostate 19:91–98.
6. Gkonos, P J, Krongrad, A, & Roos, B A (1995). Neuroendocrine peptides in the prostate [editorial]. Urol. Res. 23:81–87.
7. Ahlgren, G, Pedersen, K, Lundberg, S, Aus, G, Hugosson, J, & Abrahamsson, P-A (2000). Neuroendoocrine differentiation is not prognostic of failure after radical prostatectomy but correlates with tumor colume. Urology 56:1011–1015.
8. Cussenot, O, Villette, J M, Cochand-Priollet, B, & Berthon, P (1998). Evaluation and clinical value of neuroendocrine differentiation in human prostatic tumors. Prostate Suppl. 8:43–51.
9. Di Santi'Agnese, P A (1998). Neuroendocrine cells of the prostate and neuroendocrine differentiation in prostatic carcinoma: a review of morphologic aspects. Urology 51:121–124.
10. Di Santi'Agnese, P A (1998). NE differentiation in prostatic carcinoma. Prostate Suppl. 8, 74–79.
11. Jiborn, T, Bjartell, A, & Abrahamsson, P A (1998). Neuroendocrine differentiation in prostatic carcinoma during hormonal treatment. Urology 51:585–589.
12. Aprikian, A G, Han, K, Guy, L, Landry, F, Begin, L R, & Chevalier, S (1998). NE differentiation and the bombesin/gastrin-releasing peptide family of neuropeptides in the progression of human prostate cancer. Prostate Suppl. 8:52–61.
13. Sehgal, I, Powers, S, Huntley, B, Powis, G, Pittelkow, M, & Maihle, N J (1994). Neurotensin is an autocrine trophic factor stimulated by androgen withdrawal in PCA. PNAS 91:4673–4677.
14. Bonkhoff, H, & Remgerger, K (1996). Differentiation pathways and histogenetic aspects of normal and abnormal prostatic growth: a stem cell model. Prostate 28:98–106.
15. Bang, Y J, Pirnia, F, Fang, W G, Kang, W K, Sartor, O, Whitesell, L, Ha, M J, Tsokos, M, Sheahan, D, Nguyen, P, Niklinski, W T, Myers, C E, & Trepel, J B (1994). Terminal neuroendocrine differentiation of human prostate carcinoma cells in response to increased intracellular cyclic AMP. Proc. Natl. Acad. Sci. USA 91:5330–5334.
16. Shen, R, Dorai, T, Szaboles, M, Katz, A, Olsson, C A, & Buttyan, R (1997). Trans-differentiation of cultured human prostate cancer cells to a neuroendocirine cell phenotype in a hormone-depleted medium. Urol. Oncol. 3:67–75.
17. Qiu, Y, Robinson, D, Pretlow, T G, & Kung, H J (1998). Etk/Bmx, a tyrosine kinase with a pleckstrin-homology domain, is an effector of phosphatidylinositol 3'-kinase and is involved in interleukin 6-induced neuroendocrine differentiation of prostate cancer cells. PNAS USA 95:3644–3649.
18. Cox, M E, Deebe, P D, Lakhani, S, & Parsons, S (1999). Acquisition of neuroendocrine characteristics by prostate tumor cells is reversible: Implications for prostate cancer progression. Cancer Res. 59:3821–3830.
19. Lin, M F, Meng, T C, Rao, P, Chang, C S, Schonthal, A H, & Lin, F F (1998). Expression of human prostatic acid phosphatase correlates with androgen-stimulated cell proliferation in prostate cancer cell lines. J. Biol. Chem. 273:5939–5947.
20. Meng, T C, Lee, M S, & Lin, M F (2000). Interaction between protein tyrosine phosphatase and protein tyrosine kinase is involved in androgen-promoted growth of human prostate cancer cells. Oncogene 19:2664–2677.
21. den Hertog, J, Pals, C E, Peppelenbosch, M P, Tertoolen, L G, de Laat, S W, Kruijer, W (1993). RPTPαlpha activates pp60c-src and is involved in neuronal differentiation. EMBO J. 12:3789–3798.
22. Bjelfman, C, Meyerson, G, Cartwright, C A, Mellstrom, K, Hammerling, U, & Pahlman, S (1990). Early activation of endogenous pp60src kinase activity during neuronal differentiation of cultured human neuroblastoma cells. Mol. Cell. Biol. 10:361–370.
23. Lynch, S A, Brugge, J S, & Levine, J M (1986). Induction of altered c-src product during neural differentiation of embryonal carcinoma cells. Science 234:873–876.
24. van Inzen, W G, Peppelenbosch, M P, van den Brand, M W, Tertoolen, L G, & de Laat, S (1996). The role of receptor protein tyrosine phosphatase alpha in neuronal differentiation of embryonic stem cells. Brain Res. Dev Brain Res. 91:304–307.
25. Yang, X H, Seow, K T, Bahri, S M, Oon, S H, & Chia, W (1991). Two Drosophila receptor-like tyrosine phosphatase genes are expressed in a subset of developing axons and pioneer neurons in the embryonic CNS. Cell 67:661–673.
26. Zelivianski, S, Dean, J, Madhavan, D, Lin., F F, & Lin, M F (2000). Expression of receptor protein tyrosine phosphatase a mRNA in human prostate cancer cell lines. Mol. Cellu. Biochem. 208:11–18.
27. Sap, J, Eustachio, P D, Givol, D, & Schlessinger, J (1990). Cloning and expression of a widely expressed receptor tyrosine phosphatase. Proc. Natl. Acad. Sci. USA 87:6112–6116.
28. Daum, G, Regenass, S, Sap, J, Schlessinger, J, & Fischer, E H (1994). Multiple forms of the human tyrosine phosphatase RPTPα. Isozymes and differences in glycosylation. J.Biol.Chem.269, 10524–28.
29. Dixon, S C, Knopf, K B, & Figg, W D (2001). The control of prostate-specific antigen expression and gene regulation by pharmacological agents. Pharmacol Rev 53:73–91.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:
1. A human prostate cancer-associated neuroendocrine (NE)-like cell line NE-1-3, deposited at ATCC under accession number PTA-3568.
2. A human prostate cancer-associated neuroendocrine (NE)-like cell line NE-1-8, deposited at ATCC under accession number PTA-3569.

* * * * *